US011007067B2

(12) United States Patent
Masson et al.

(10) Patent No.: US 11,007,067 B2
(45) Date of Patent: *May 18, 2021

(54) EXPANDABLE SPINAL FUSION CAGE

(71) Applicant: Sidewinder Medical Products LLC, Coral Springs, FL (US)

(72) Inventors: Robert Masson, Windermere, FL (US); James Scott Hay, Parkland, FL (US); Ryan Singh, Loxahatchee, FL (US)

(73) Assignee: Sidewinder Medical Products LLC, Coral Springs, FL (US)

( * ) Notice: Subject to any disclaimer, the term of this patent is extended or adjusted under 35 U.S.C. 154(b) by 46 days.

This patent is subject to a terminal disclaimer.

(21) Appl. No.: 16/441,546

(22) Filed: Jun. 14, 2019

(65) Prior Publication Data

US 2019/0290446 A1 Sep. 26, 2019

Related U.S. Application Data

(63) Continuation of application No. 15/213,477, filed on Jul. 19, 2016, now Pat. No. 10,322,007, which is a (Continued)

(51) Int. Cl.
*A61F 2/44* (2006.01)
*A61B 17/86* (2006.01)
(Continued)

(52) U.S. Cl.
CPC .......... *A61F 2/446* (2013.01); *A61B 17/863* (2013.01); *A61F 2/4455* (2013.01); *A61B 17/70* (2013.01);
(Continued)

(58) Field of Classification Search
None
See application file for complete search history.

(56) References Cited

U.S. PATENT DOCUMENTS 6,019,793 A * 2/2000 Perren ............... A61F 2/442
623/17.16
8,512,409 B1 * 8/2013 Mertens ............ A61F 2/447
623/17.16

(Continued)

FOREIGN PATENT DOCUMENTS

WO WO-2008044057 A1 * 4/2008 .......... A61F 2/4465

*Primary Examiner* — Jan Christopher L Merene
(74) *Attorney, Agent, or Firm* — Nicholas R. Lewis, P.A.

(57) ABSTRACT

A device, system, and method for performing a spinal procedure. The device includes first and second shape-memory outer platforms, the outer platforms expanding at a temperature greater than the transformative temperature, a core member having first and second expansion bodies and first and second wedge members, the first expansion body being coupled to the first outer platform and the second expansion body being coupled to the second outer platform, and a screw rotatably disposed within the core member, the screw passing through at least a portion of each of the first and second wedge members. Rotation of the screw causes the first and second wedge members to move toward each other and the first and second expansion bodies to move away from each other. Thus, reaching a transformation temperature and rotating the screw expands the device to come in contact with and anchored against both of the adjacent vertebrae.

16 Claims, 12 Drawing Sheets

Related U.S. Application Data continuation of application No. 14/258,149, filed on Apr. 22, 2014, now Pat. No. 9,421,110.

(60) Provisional application No. 61/821,987, filed on May 10, 2013.

(51) Int. Cl.
    *A61F 2/46*     (2006.01)
    *A61F 2/30*     (2006.01)
    *A61B 17/70*     (2006.01)

(52) U.S. Cl.
CPC ..... *A61F 2/4611* (2013.01); *A61F 2002/3023* (2013.01); *A61F 2002/30092* (2013.01); *A61F 2002/30224* (2013.01); *A61F 2002/30289* (2013.01); *A61F 2002/30387* (2013.01); *A61F 2002/30405* (2013.01); *A61F 2002/30411* (2013.01); *A61F 2002/30433* (2013.01); *A61F 2002/30484* (2013.01); *A61F 2002/30545* (2013.01); *A61F 2002/30556* (2013.01); *A61F 2002/30568* (2013.01); *A61F 2002/30579* (2013.01); *A61F 2002/30622* (2013.01); *A61F 2002/30884* (2013.01); *A61F 2002/30891* (2013.01); *A61F 2002/30904* (2013.01); *A61F 2220/0016* (2013.01); *A61F 2310/00023* (2013.01)

(56) References Cited

U.S. PATENT DOCUMENTS

2003/0065396 A1* 4/2003 Michelson ............ A61F 2/4611
                                              623/17.15
2007/0239278 A1* 10/2007 Heinz ................... A61F 2/4425
                                              623/17.15

* cited by examiner

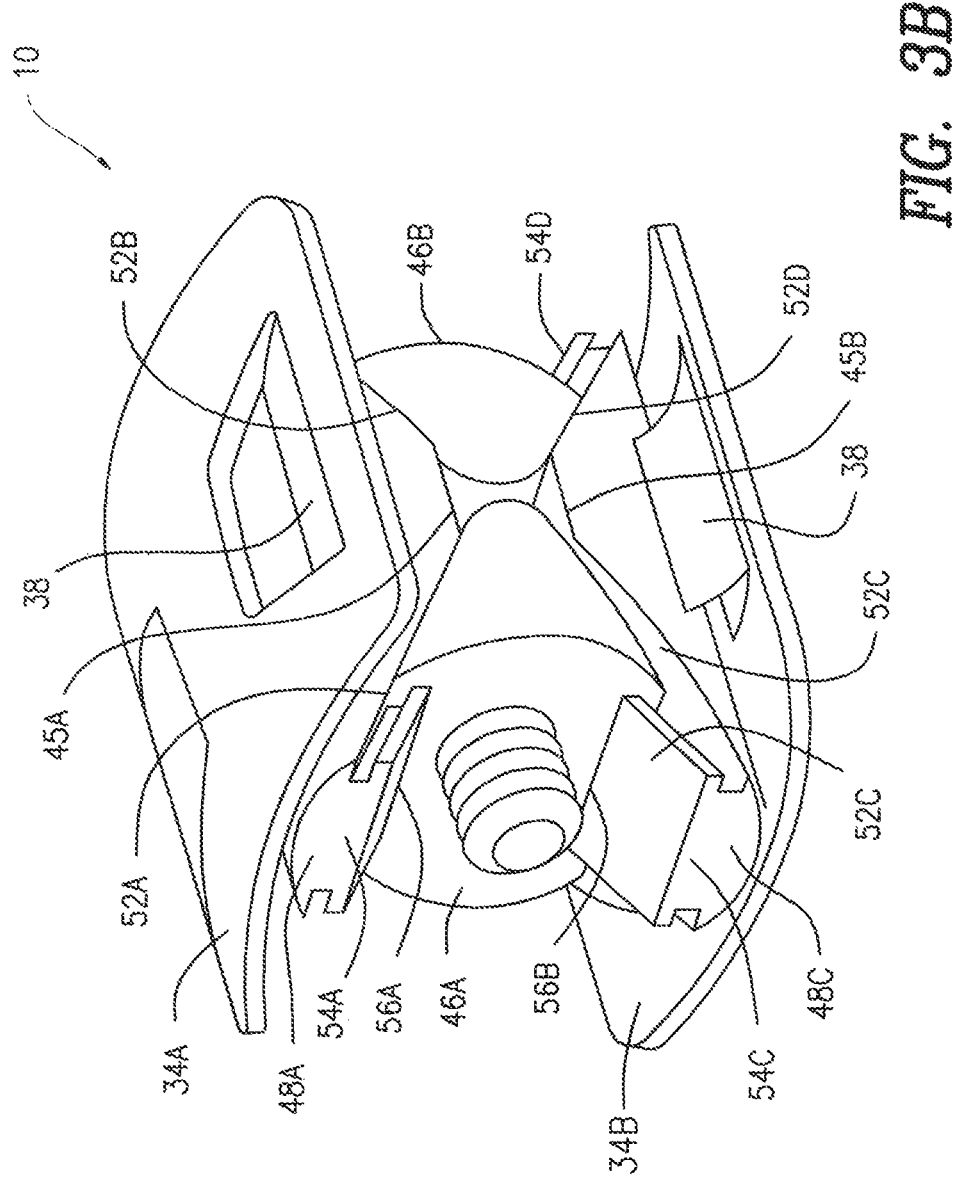

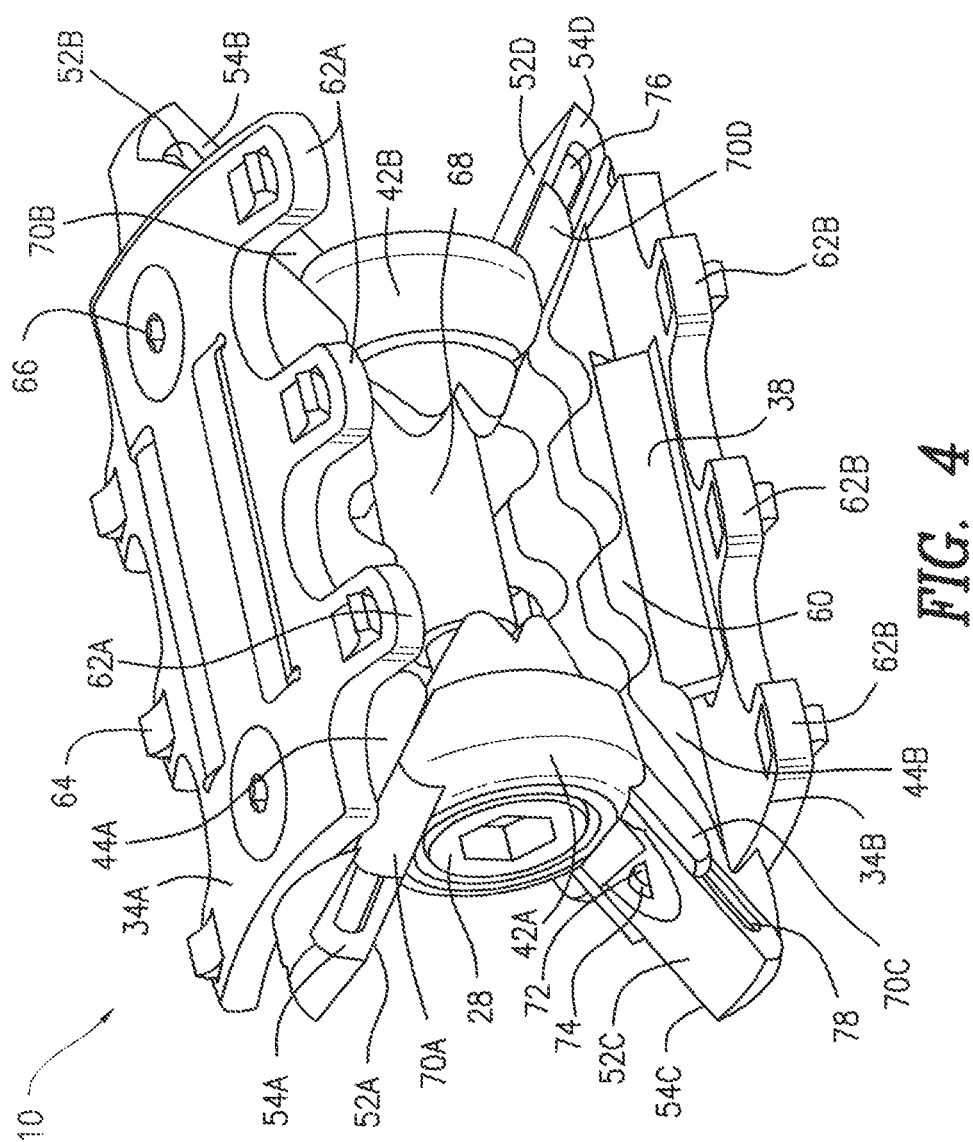

EXPANDABLE SPINAL FUSION CAGE

CROSS-REFERENCE TO RELATED APPLICATION

This is a continuation of U.S. patent application Ser. No. 15/213,477, filed Jul. 19, 2016, entitled EXPANDABLE SPINAL FUSION CAGE, which is a continuation of U.S. patent application Ser. No. 14/258,149, filed Apr. 22, 2014, entitled EXPANDABLE SPINAL FUSION CAGE, which is related to and claims priority to U.S. Provisional Patent Application Ser. No. 61/821,987, filed May 10, 2013, entitled EXPANDABLE SPINAL FUSION CAGE, the entirety of all of which is incorporated herein by reference.

STATEMENT REGARDING FEDERALLY SPONSORED RESEARCH OR DEVELOPMENT n/a

FIELD OF THE INVENTION

The present invention relates to a method, system, and device for performing spinal fusion procedures with minimal anatomical manipulation. Specifically, the present invention relates to a method, system, and device for preparing an intervertebral space for spinal fusion or other medical procedure, implanting a device such as an expandable spine cage, and/or introducing and depositing material such as bone graft material, stem cells, antibiotic, and the like to an intervertebral space.

BACKGROUND OF THE INVENTION

Spinal fusion (also called spondylodesis or spondylosyndesis) is a surgical procedure by which two or more adjacent vertebrae are joined or fused together. This method is primarily used to reduce or eliminate pain caused by abnormal motion of the vertebrae from conditions such as scoliosis, degenerative disc disease, spondylolisthesis, kyphosis, spinal stenosis, fractures, infections, tumors, and other degenerative spinal conditions or conditions that cause instability of the spine.

In interbody fusion, a commonly performed type of spinal fusion, a medical device called an interbody fusion cage or spine cage is surgically inserted between adjacent vertebrae to maintain spine alignment and disc height. Additionally, graft material harvested from the patient (autograft) or from a donor (allograft) is inserted into the intervertebral space with the spine cage to encourage the natural osteoblastic process and resulting fusion between the endplates of the vertebrae. Pedicle screws may also be used to augment the fusion.

Interbody fusion methods that access the vertebrae through the patient's back (rather than an anterior approach through the abdomen), such as the posterior transpedicular approach, typically involves muscle dissection from the back of the spine in order to create enough space to insert one or two spine cages. The spine cage has a diameter that is equal to the desired distance by which the vertebrae are to be separated, and so significant manipulation of the anatomy surrounding the vertebrae must be performed. Not only are the spinal muscles stretched, moved, or cut, but parts of the ligament flava, which connect the laminae of the adjacent vertebrae, around the implantation site are cut away from the laminae and removed. Additionally, parts of the laminae and/or pedicle above and below, and parts of the facet joints on either side, of the implantation site are removed to increase access. Finally, a substantial portion of the intervening disc is removed and the endplates of the adjacent vertebrae rasped or roughened.

Unsurprisingly, the posterior transpedicular approach is very traumatic to the patient. Not only is there a long recovery time, but the patient may experience significant amounts of pain immediately following the procedure. Further, the procedure compromises the ligaments and muscles that aid in spinal stability, strength, and function. Other known procedures, such as transforaminal interbody fusion methods (TLIF), posterior lumbar interbody fusion methods (PLIF), and lateral and anterolateral transpsoas fusion methods may be equally traumatic to the patient. For example, such procedures may easily result in nerve, ligament, bone, and/or soft tissue damage.

It is therefore desirable to provide a spinal implantation device and method that requires less anatomical manipulation, a smaller insertion space, and is less traumatic than currently known methods.

SUMMARY OF THE INVENTION

The present invention advantageously provides a method, device, and system for spinal medical procedures that require less anatomical manipulation, a smaller insertion space, and is less traumatic than currently known methods. In one non-limiting embodiment, an intervertebral medical device may include a core member, a screw rotatably disposed within the core member, and a first outer plate and a second outer plate, each of the first and second outer plates being coupled to at least a portion of the core member. The first and second outer plates may be composed of a shape memory material, and may be transitionable between a non-expanded configuration and an expanded configuration. For example, the first and second outer plates may transition to the expanded configuration when the temperature of the first and second outer plates is greater than a transformative temperature of the shape memory material. The core member may include a first expansion body coupled to the first outer plate and a second expansion body coupled to the second outer plate and a first wedge member and a second wedge member, the screw extending through at least a portion of the first and second wedge member. The core member may further include a sleeve coupled to one of the first and second wedge members, the sleeve defining a first expansion guide and a second expansion guide, the screw extending through at least a portion of the sleeve. The first and second expansion guides may extend from the sleeve in opposite directions, the first expansion guide extending toward the first outer plate and the second expansion guide extending toward the second outer plate. Further, each expansion guide may include a substantially diagonal edge, at least a portion of each expansion guide defining a slot that is substantially parallel to the diagonal edge. Rotation of the screw may cause the core member to transition from a first configuration to a second configuration, during which transition the first and second wedge members may move closer to each other and the first and second expansion bodies may move away from each other. The device may further include a first tissue engagement element and a second tissue engagement element; and a first center expansion arm hingedly connected to the first tissue engagement element and a second center expansion arm hingedly connected to the second tissue engagement element, the first center expansion arm being receivable within the slot of the first expansion guide and the second center expansion arm being receivable within the slot of the second expansion guide when the core member is transitioned from the first configuration to the second configuration. Each of the first and second outer plates may define an opening, the first and second tissue engagement elements extending through a corresponding opening when the device is in the second configuration. Each expansion body may define a first diagonal portion, a second diagonal portion, and a center portion, the center portion being substantially horizontal relative to the first and second diagonal portions. At least a portion of the first wedge may be in contact with and slidable relative to the first diagonal portion of the each of the first and second expansion bodies, and at least a portion of the second wedge may be in contact with and slidable relative to the second diagonal portion of each of the first and second expansion bodies. Further, each diagonal portion may include a ridge and each wedge includes a first groove and a second groove, the ridge of each diagonal portion being matable with a corresponding of the first and second grooves. Each wedge may include a locking mechanism that has a protrusion and each ridge includes at least one opening, the protrusion being engageable with the at least one opening of a corresponding ridge.

In another non-limiting embodiment, a medical device for insertion between two adjacent vertebrae may include: a first outer platform and a second outer platform, each of the first and second outer platforms being composed of a shape-memory material having a transformative temperature, the device being in a first configuration at a first temperature and being in a second configuration at a second temperature, the second temperature being greater than the transformative temperature; a core member including a first expansion body, a second expansion body, a first wedge member, and a second wedge member, the first expansion body being coupled to the first outer platform and the second expansion body being coupled to the second outer platform; and a screw rotatably disposed within the core member, the screw passing through at least a portion of each of the first and second wedge members, rotation of the screw causing the first and second wedge members to move toward each other and the first and second expansion bodies to move away from each other. The core member may further include a sleeve coupled to one of the first and second wedge members and disposed about at least a portion of the screw. Further, the sleeve may define a first expansion guide and a second expansion guide, the first and second expansion guides extending from the sleeve in opposite directions, the first expansion guide extending toward the first outer plate and the second expansion guide extending toward the second outer plate, each expansion guide including a substantially diagonal edge, at least a portion of each expansion guide defining a slot that is substantially parallel to the diagonal edge. The device may further include a first tissue engagement element and a second tissue engagement element; and a first center expansion arm hingedly connected to the first tissue engagement element and a second center expansion arm hingedly connected to the second tissue engagement element, the first center expansion arm being receivable within the slot of the first expansion guide and the second center expansion arm being receivable within the slot of the second expansion guide when the first and second wedge members move toward each other causing the device to transition to an expanded configuration, each of the first and second outer plates defining an opening, the first and second tissue engagement elements extending through a corresponding opening when the device is in the expanded configuration.

In one non-limiting embodiment, a system for interbody spinal fusion may include a medical device including a core member, a screw rotatably disposed within the core member, and a first outer plate and a second outer plate, each of the first and second outer plates being coupled to at least a portion of the core member, rotation of the screw transitioning the medical device between a non-expanded configuration and an expanded configuration. The system may further include an insertion device including a lumen sized to accommodate the medical device therein when the medical device is in the non-expanded configuration.

In one non-limiting embodiment, a method of performing a medical procedure in an intervertebral space may include positioning a medical device in the intervertebral space, the medical device including: a core member; a screw rotatably disposed within the core member, rotation of the screw in a first direction causing the core member to expand and rotation of the screw in a second direction causing the core member to contract; and a first outer plate and a second outer plate each being composed of a shape-memory material having a transformation temperature, and each being coupled to at least a portion of the core member, a temperature within the intervertebral space being greater than the transformation temperature and causing the first and second outer plates to transition from a substantially curved configuration to a substantially flat configuration; and rotating the screw to expand the core member until each of the first and second outer plates is in contact with a portion of a vertebra.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3B shows the second embodiment of a spine cage in a fully expanded state;

FIG. 4 shows a third embodiment of a spine cage in a fully expended state;

DETAILED DESCRIPTION OF THE INVENTION

Figure 1A:
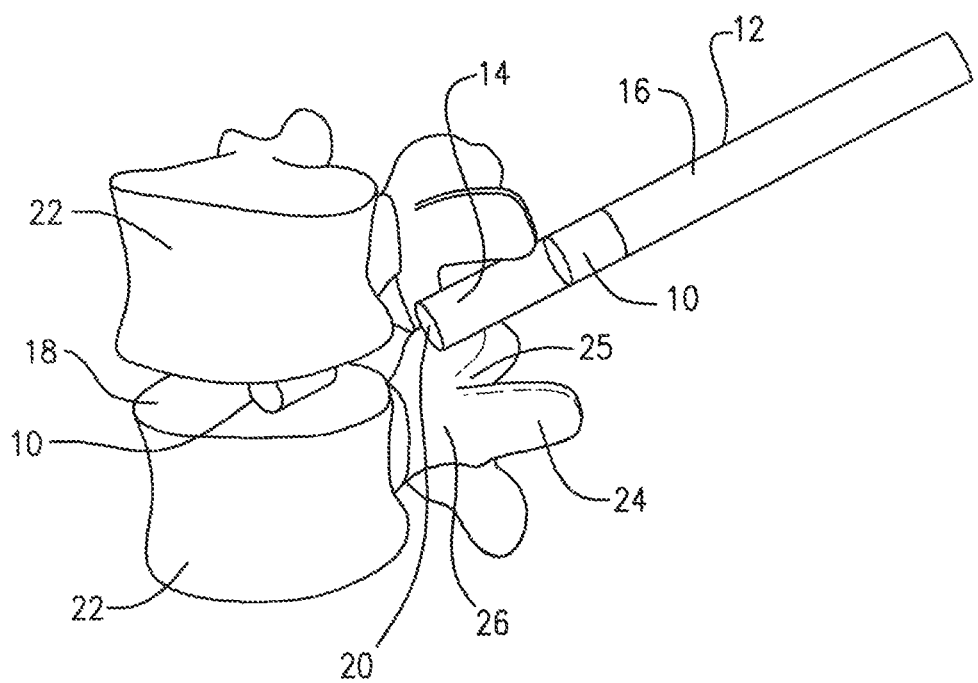
FIG. 1A shows a first access pathway to an intervertebral space, such as for the insertion of a spine cage.
Figure 1B:
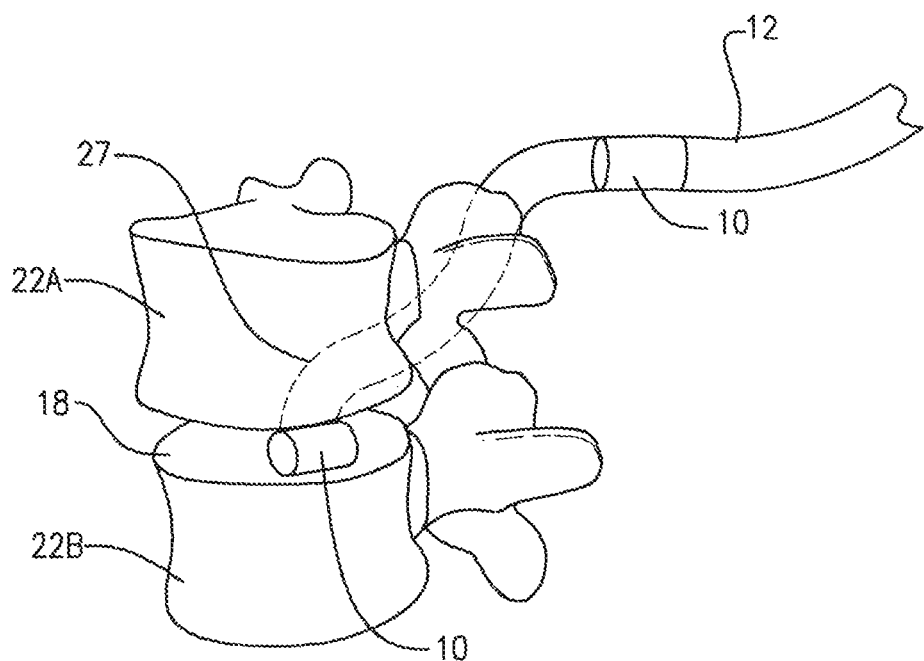
FIG. 1B shows a second access pathway to an intervertebral space, such as for the insertion of a spine cage.

The present invention relates to a method, system, and device for performing spinal fusion procedures with minimal anatomical manipulation. Referring now to the drawings in which like reference designators refer to like elements, FIGS. 1A and 1B show insertion of an expandable spine cage. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the device and system disclosed herein may be included in a variety of different combinations or configurations without departing from the scope and spirit of the invention.

Continuing to refer to FIGS. 1A and 1B, insertion of an expandable spine cage is shown. The system for insertion of a spine cage used in an interbody fusion procedure generally includes a spine cage 10 and an insertion device 12. The spine cage 10 may be transitionable from an unexpanded state to an expanded state, and shown and described in greater detail in FIGS. 2A-5B. The insertion device 12 may be a cannula having an elongate, rigid distal portion 14 defining a lumen 16 sized to accommodate the diameter of the spine cage 10 in an unexpanded state (for example, as shown in FIG. 1A) and to be positioned proximate an intervertebral space 18 for delivery of the spine cage 10. Alternatively, the insertion device 12 may be a cannula-like device having an elongate, flexible distal portion defining a lumen 16 sized to accommodate the diameter of the spine cage 10 in an unexpanded state (for example, as shown in FIG. 1B). In this embodiment, the flexible distal portion 14 of the insertion device 12 may be steerable to allow for complete site preparation before a medical procedure or precise positioning of a spine cage and/or graft material, stem cells, or other materials or devices. As a non-limiting example, the distal portion 14 may be steered using one or more pull wires, push rods, or other steering mechanisms. In either embodiment, the distal portion 14 of the insertion device 12 may be free of texture to reduce tissue, ligament, and/or bone damage in the area proximate the implantation site. Further, the insertion device may include an opening 20 at the distal tip of the elongated portion through which the spine cage 10 may be expelled.

The method may generally include placing the insertion device 12 proximate the space 18 between the adjacent vertebrae 22 to be fused. For example, the insertion device 12 may be inserted posteriorly, for example, between the transverse processes 24 or laminae 25 of adjacent target vertebrae 22. Once the distal tip 14 of the insertion device 12 is adjacent to the intervertebral space 18, the insertion device 12 may be used to expel the spine cage 10 into the intervertebral space 18. For example, the spine cage 10 may be expelled from the insertion device 12 using a push rod, air pressure, hydraulic pressure, or other suitable means. Additionally, an insertion device 12 having a steerable distal portion 14, such as that shown in FIG. 1B, may be inserted in a unique manner, such as from a pedicle 26 of a first vertebra 22A into the intervertebral space 18 between the first vertebra 22A and an adjacent vertebra 22B (as shown in FIG. 1B). Unlike currently known methods that simply use a linear pathway (for example, a linear pathway following the trajectory of a pedicle), this pathway avoids damaging the dura matter, spinal cord, or other sensitive non-target tissue while still allowing access to the intervertebral space within minimal anatomical manipulation. Further, the flexible insertion device 12 may be used to introduce tools for preparing the intervertebral space for a medical procedure. For example, the insertion device 12 may be used to introduce a flexible screw bit to produce an access pathway from a pedicle of one vertebra to the intervertebral space between the first vertebra and an adjacent vertebra. The steerable distal portion 14 of the insertion device 12 allows the user to create a curved or twisted pathway suitable for an individual patient's anatomy and/or treatment needs. Once the pathway is drilled, the insertion device may be used to implant a device such as a spine cage 10 and/or to introduce or deposit biological or non-biological materials such as bone graft material, stem cells, antibiotics, plugs, or other materials. Further, this pathway 27 may be used to introduce or deposit such materials over the course of an extended treatment period (for example, twelve or sixteen weeks), such as a treatment period following spine cage implantation during which stem cells are deposited to encourage disc regeneration.

As mentioned, the insertion device 12 may be used for spine cage implantation with minimal anatomical manipulation. The spine cage 10 (such as those shown in FIGS. 2A-5B) may be inserted into the body in its unexpanded state, which has a diameter that may be significantly smaller than currently used spine cages. For example, the diameter of the spine cage 10 in the unexpanded state may be such that the spine cage 10 may be used within an insertion device lumen 16 having an approximately 8 mm diameter. As a non-limiting example, the spine cage 10 may have a diameter in the unexpanded state of approximately 7 mm. Consequently, other than removal of at least a portion of the vertebral disc, the present method requires only minimal manipulation and/or removal of the spinal muscles, ligaments, and/or bone, if any, to accommodate the insertion device and spine cage 10.

Figure 2A:
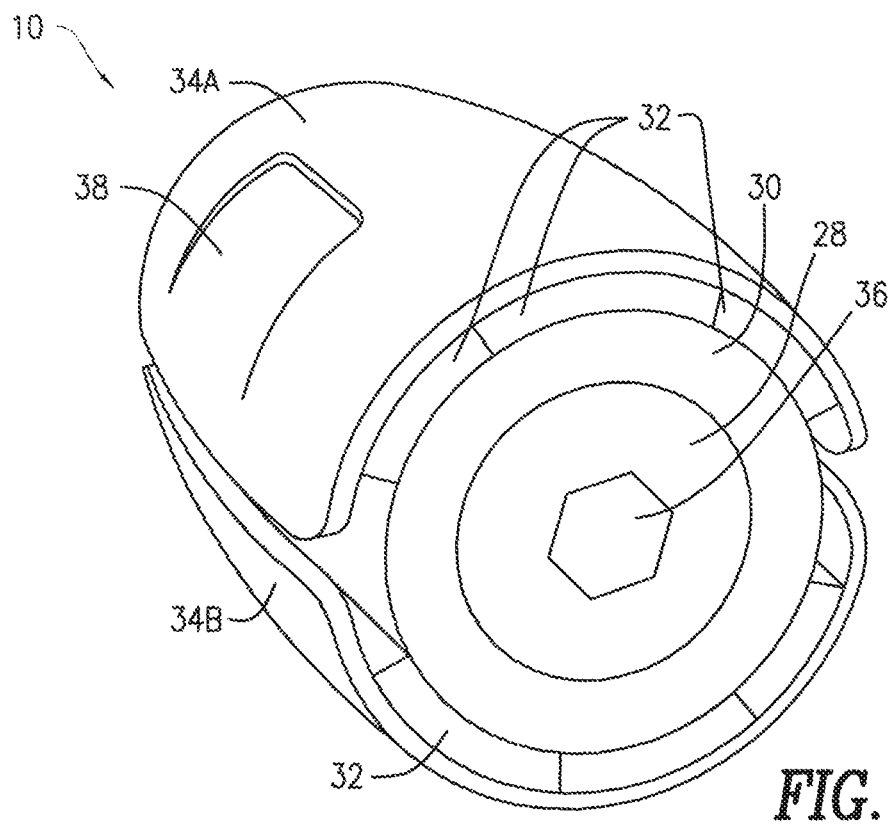
FIG. 2A shows a first embodiment of a spine cage in an unexpanded state.

Referring now to FIG. 2A, a first embodiment of a spine cage 10 in an unexpanded state is shown. The spine cage 10 may generally include an expansion screw 28, a core member 30, a plurality of cam plates 32, and first 34A and second 34B outer shape memory platforms. In the unexpanded configuration, the cam plates 32 may be in contact with the core member 30 and each of the first 34A and second 34B platforms may be in contact with at least one of the plurality of cam plates 32. In other words, the cam plates 32 may be sandwiched between the core member 30 and platforms 34A, 34B. As a non-limiting example, the diameter of the spine cage 10 may be approximately 8 mm or less.

The core member 30 may have a tubular configuration, and the expansion screw 28 may be rotatably disposed within the core member 30. Further, the expansion screw 28 may have a hexagonal socket 36 in at least one end. The expansion screw 28, core member 30, and cam plates 32 may be composed of a rigid, durable, biocompatible material such as titanium. The outer platforms 34A, 34B, on the other hand, may be composed of a shape memory material such as Nitinol.

Figure 2B:
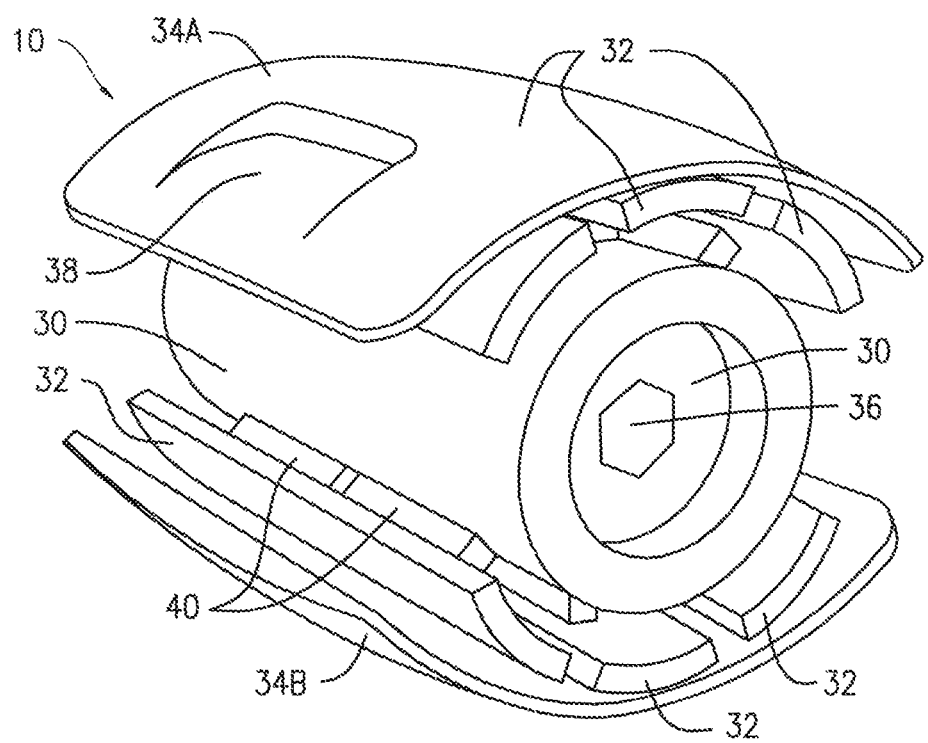
FIG. 2B shows the first embodiment of a spine cage in an expanded state.

Referring now to FIG. 2B, a first embodiment of a spine cage 10 in an expanded state is shown. The shape memory platforms 34A, 34B may be manufactured such that the platforms have an original position as shown in the expanded configuration of FIG. 2B, and a deformed position with greater curvature, as shown in the unexpanded configuration of FIG. 2A. Once the spine cage 10 has been inserted in the intervertebral space 18, the higher body temperature of the surrounding area may be above the transformation temperature of the shape memory material, thereby causing the platforms 34A, 34B to flatten out and/or unfold. This unfolding creates a wider footprint than the spine cage in the unexpanded state, which can add stability to the implant and provide a larger surface area engagement with the superior endplate of one vertebra and the inferior endplate of another vertebra (that is, the endplates of the vertebrae between which the spine cage is positioned). Additionally, each platform 34A, 34B may include at least a portion 38 that has a different present shape memory configuration, such that these portions function as support arms to displace the load (e.g., compressive force of the spine) from the platforms to the vertebral endplates (as shown in FIG. 2B). Further, each platform 34A, 34B may include one or more spikes or protrusions (for example, as shown in FIG. 4 as reference number 64) that expand or are exposed as the shape memory platforms expand. These spikes or protrusions may enhance grip between the platforms and the vertebral endplates.

Even though the unfolding of the shape memory platforms enhances contact between the spine cage 10 and adjacent vertebrae 22, this expansion may not provide sufficient distractive force between the vertebrae. In fact, it is not intended that the unfolding do so, as this may cause uncontrolled distraction. So, the cam plates 32 may be expanded to provide a controlled gross distraction between adjacent vertebrae 22. To expand the cam plates 32, a tool may be matably inserted into the hexagonal socket 36 of the expansion screw 28 and rotated (for example, in the clockwise direction). The tool may be sized to be inserted into the access pathway 27 created for the insertion device 12. The expansion screw 28 may include eccentric threading on at least a portion of its outer surface, such that rotation of the expansion screw 28 will advance the eccentric threading farther into the core member 30, displacing one or more cams 32 or base plates 40 coupled to the cam plates 32. Thus, rotational motion of the expansion screw 28 is translated into linear movement (e.g., outward movement) of the cam plates 32. The expansion screw 28 may be rotated, and the spine cage expanded, until the surgeon is satisfied that there is sufficient contact between the outer platforms 34A, 34B and the vertebral endplates and/or that the vertebrae are sufficiently distracted.

One or more additional spine cages 10 may likewise be inserted in the intervertebral space 18. Once the one or more spine cages 10 have been implanted in the target site, graft material may be added to the intervertebral space surrounding the one or more spine cages. Closing the insertion pathway 27 may be significantly easier and less traumatic than in currently known methods of interbody spinal fusion, and less, if any, bone removal is required (for example, removal of portions of the pedicles and/or laminae), thereby greatly facilitating patient recovery time.

Figure 3A:
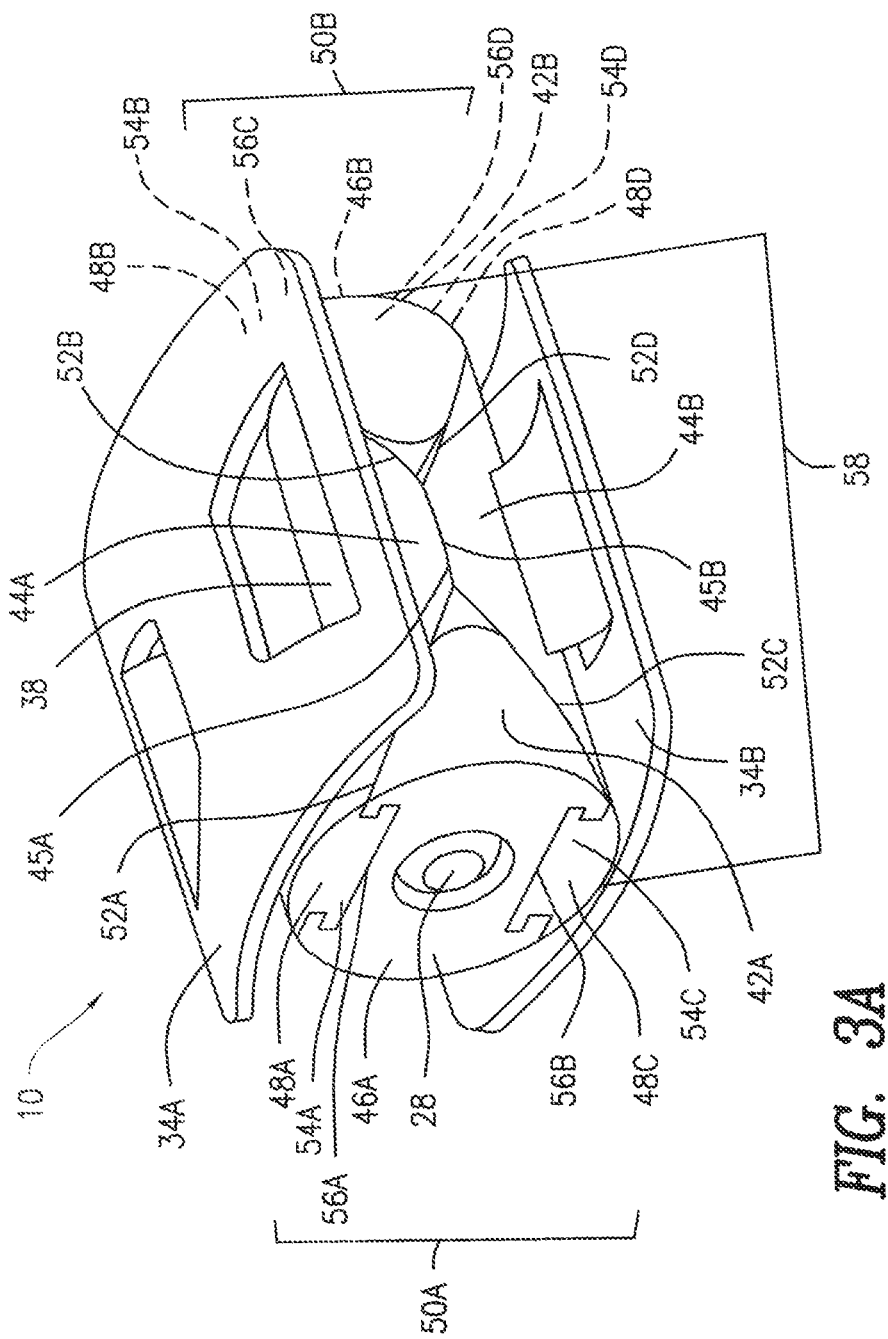
FIG. 3A shows a second embodiment of a spine cage in a partially expanded state.

Referring now to FIG. 3A, a second embodiment of a spine cage 10 in a partially expanded state is shown. The spine cage 10 may generally include an expansion screw 28, first 42A and second 42B wedges, first 44A and second 44B expansion bodies, and first 34A and second 34B outer shape memory platforms. The first 42A and second 42B wedges and first 44A and second 44B expansion bodies may together make up the core member 58. In the unexpanded or partially expanded configurations, the first and second expansion bodies 44A, 44B are in contact with each other, whereas the first and second wedges 42A, 42B are a distance apart from each other. For example, the first expansion body 44A may include a flat portion 45A that is in contact with the flat portion 45B of the second expansion body 44B. Further, each of the wedges 42A, 44B may include an outer face 46A, 46B and each of the expansion bodies 44A, 44B may include a first 48A, 46C and second 48B, 48D outer face (obscured from view). When in the unexpanded or partially expanded configuration, the outer face 46A of the first wedge 42A may be coplanar with the first outer face 48A of the first expansion body 44A and the first outer face 48C of the second expansion body 44B, so as to create a first surface 50A that is substantially circular. Likewise, when in the unexpanded or partially expanded configuration, the outer face 46B of the second wedge 42B may be coplanar with the second outer face 48B of the first expansion body 44A and the second outer face 48D of the second expansion body 44B, so as to create a second surface 50B that is substantially circular. Further, each expansion body 44A, 44B may include a substantially V-shaped cross section that includes two diagonal portions 52A, 52B, 52C, 52D, with each diagonal portion including a flange 54A, 54B, 54C, 54D (54B and 54D obscured from view) that fits within and is slidably disposed within a complementary groove 56A, 56B, 56C, 56D (56B and 56D obscured from view) of the adjacent wedge 42A, 42B.

The first and second wedges 42A, 42B and first and second expansion bodies 44A, 44B together may create a core member 58 that is substantially tubular in shape, and the expansion screw 28 may be rotatably disposed within the core member 58. For example, the expansion screw 28 may extend through at least a portion of each of the first 42A and second 42B wedges. Further, the expansion screw 28 may have a hexagonal socket, knob, or other configuration in at least one end (obscured from view), for example, as shown in FIGS. 2A and 2B. Rotation of the expansion screw 28 in a first direction may cause the core member 58 to expand, and rotation of the expansion screw 28 in a second direction may cause the core member 58 to contract. The expansion screw 28 and core member 58 may be composed of a rigid, durable, biocompatible material such as titanium. The outer platforms 34A, 34B, on the other hand, may be composed of a shape memory material such as Nitinol. In the partially expanded configuration shown in FIG. 3A, the shape memory platforms 34A, 34B may be expanded (for example, as a result in the temperature increase when the spine cage is implanted within the patient's body), but the core member 58 is unexpanded. In the unexpanded state, the spine cage of FIGS. 3A and 3B may resemble the unexpanded spine cage shown in FIG. 2A.

Referring now to FIG. 3B, a second embodiment of a spine cage 10 in an expanded state is shown. As shown in FIG. 3A, the shape memory platforms 34A, 34B may be manufactured such that the platforms 34A, 34B have an original position as shown in the partially expanded configuration of FIGS. 3A and 3B, and a deformed position with greater curvature (such as the unexpanded configuration of FIG. 2A), as shown and described in greater detail in FIGS. 2A and 2B. To expand the core member 58, a tool may be removably coupled to the expansion screw 28 and rotated. The tool may be inserted into the access pathway 27 created for the insertion device to access the spine cage 10 when the spine cage 10 is positioned in an intervertebral space 18. Rotation of the expansion screw 28 may draw the first and second wedges 42A, 42B toward each other, thus displacing the first and second expansion bodies 44A, 44B away from each other, as shown in FIG. 3B. As is also shown in FIGS. 3A and 3B, the flange 54A-54D of each diagonal portion 52A-52D of each expansion body 44A, 44B may be slidably disposed within the complementary groove 56A-57D of the adjacent wedge 42A, 42B. For example, the flange 54A of the first diagonal portion 52A of the first expansion body 44A and the flange 52C of the first diagonal portion 52C of the second expansion body 44B may each be slidably disposed within a first 56A and second 56B complementary groove of the first wedge 42A. Likewise, the flange 54B of the second diagonal portion 52B of the first expansion body 44A and the flange 52D of the second diagonal portion 52D of the second expansion body 44B may each be slidably disposed within a first 56C and second 56D complementary groove of the second wedge 42B. In this manner, movement of the first and second wedges 42A, 42B toward each other will displace the first and second expansion bodies 44A, 44B, and thus expand the spine cage 10. It will be understood that the flanges and complementary grooves may have any configuration suitable for expansion of the spine cage and are not limited to that shown herein. Additionally, each platform 34A, 34B may include at least a portion 38 that has a different present shape memory configuration, such that these portions function as support arms to displace the load (e.g., compressive force of the spine) from the platforms to the vertebral endplates (as shown in FIG. 3B). Further, each platform 34A, 34B may include one or more spikes or protrusions that expand or are exposed as the shape memory platforms expand. These spikes or protrusions may enhance grip between the platforms and the vertebral endplates.

Referring now to FIG. 4, a third embodiment of a spine cage 10 in an expanded state is shown. The spine cage 10 of FIG. 5 is generally similar to that shown in FIGS. 3A and 3B. However, the spine cage 10 shown in FIG. 4 may include expansion bodies 44A, 44B that each have, instead of a flattened portion, a ridged portion 60A, 60B. Further, each expansion body 44A, 44B may include a hollowed portion, such that the ridged portion 60A, 60B is composed of two individual segments, as shown in FIG. 4. Alternatively, each expansion body 44A, 44B may be solid, such that each expansion body 44A, 44B includes only one ridged portion 60A, 60B.

The outer platforms 34A, 34B of the spine cage 10 shown in FIG. 4 may be composed of a shape memory material and may also include a plurality of fingers 62A, 62B. The fingers 62A of the first outer platform 34A may be configured to be complementary to each other, such that when the spine cage 10 is in an unexpanded state and the platforms 34A, 34B are in a deformed position with greater curvature, the fingers 62A of the first outer platform 34A alternate with the fingers 62B of the second outer platform 34B. That is, at least one finger 62 of one platform 34 may be disposed between two adjacent fingers 62 of the other platform 34. The outer platforms 34A, 34B are shown in FIG. 4 in an original, expanded state. The outer platforms 34A, 34B may further include one or more spikes or protrusions 64 that expand or are exposed as the shape memory platforms 34A, 34B expand. These spikes or protrusions 64 may enhance grip between the platforms 34A, 34B and the vertebral endplates. Additionally, each platform 34A, 34B may include one or more screw conduits 66 that each extends through the platform 34 and through at least a portion of the adjacent expansion body 44. Inserting a screw into these conduits 66 may help secure the platforms 34A, 34B to the adjacent expansion body 44A, 44B. Additionally, each conduit 66 may further extend into at least a portion of a wedge 42A, 42B, and a screw inserted into the conduit 66 may provide additional locking of the spine cage 10 in an expanded configuration.

Continuing to refer to FIG. 4, the core member 58 may include two wedges 42A, 42B, each of which being engageable with the expansion screw 28 (for example, similar to that shown and described in FIGS. 3A and 3B), and a sleeve portion 68. At least one wedge 42A, 42B may include the sleeve portion 68 that extends from the wedge (42B, as shown in FIG. 4) over at least a portion of the expansion screw 28. The spine cage 10 may further include locking components 70A, 70B, 70C, 70D that are engageable with the expansion bodies 44A, 44B and the wedges 42A, 42B. Each locking component 70A-70D may include one or more protrusions 72 that are each engageable with a corresponding opening 74 on the expansion bodies 44A, 44B. As is shown and described in FIGS. 3A, and 3B, rotation of the expansion screw 28 may cause the wedges 42A, 42B to be drawn toward each other, the expansion bodies 44A, 44B are distracted from each other, thus expanding the spine cage 10. Movement of the wedges 42A, 42B relative to the diagonal portions 52A-52D of the expansion bodies 44A, 44B may cause movement of the locking components 70A-70D likewise. For example, each diagonal portion 52A-52D may include two grooves 76, and at least a portion of each locking component 70A-70D may be slidably disposed within a corresponding groove 76 in the flanges 52A-52D of the expansion bodies 44A, 44B. The protrusions 72 on the locking components 70A-70D, as they slide along the diagonal portions 52A-52D of the expansion bodies 44A, 44B, may come into contact with and fit into the corresponding openings 74 of the expansion bodies 44A, 44B, thereby locking the wedges 42A, 42B and locking components 70A, 70D in place and preventing further expansion or retraction of the wedges 42A, 42B. As shown in FIGS. 4-5C, each expansion body 44 may include a center portion located between the two diagonal portions 52, which may be substantially horizontal relative to the diagonal portions 52. The expansion bodies 44 of the device shown in FIGS. 3A and 3B may also each have a center portion between the diagonal portions 52. These center portions may be flat (for example, as shown in FIGS. 3A and 3B), textured, or including a series of troughs or other features (for example, as shown in FIG. 4).

Figure 5A:
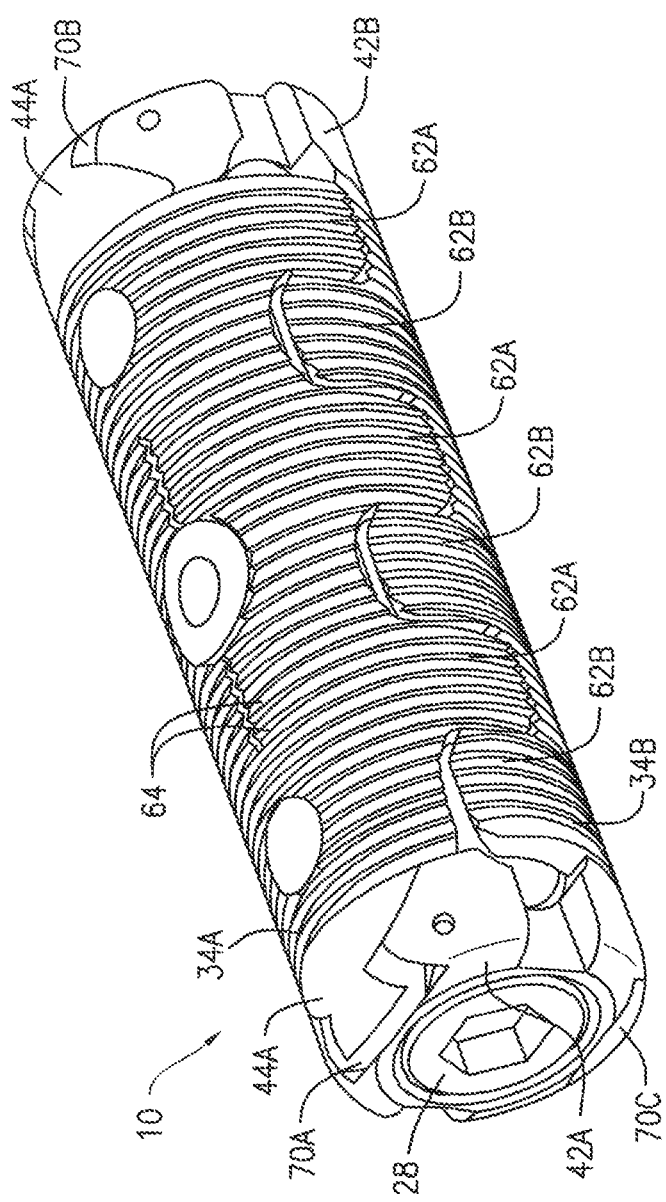
FIG. 5A shows a fourth embodiment of a spine cage in an unexpanded state.
Figure 5B:
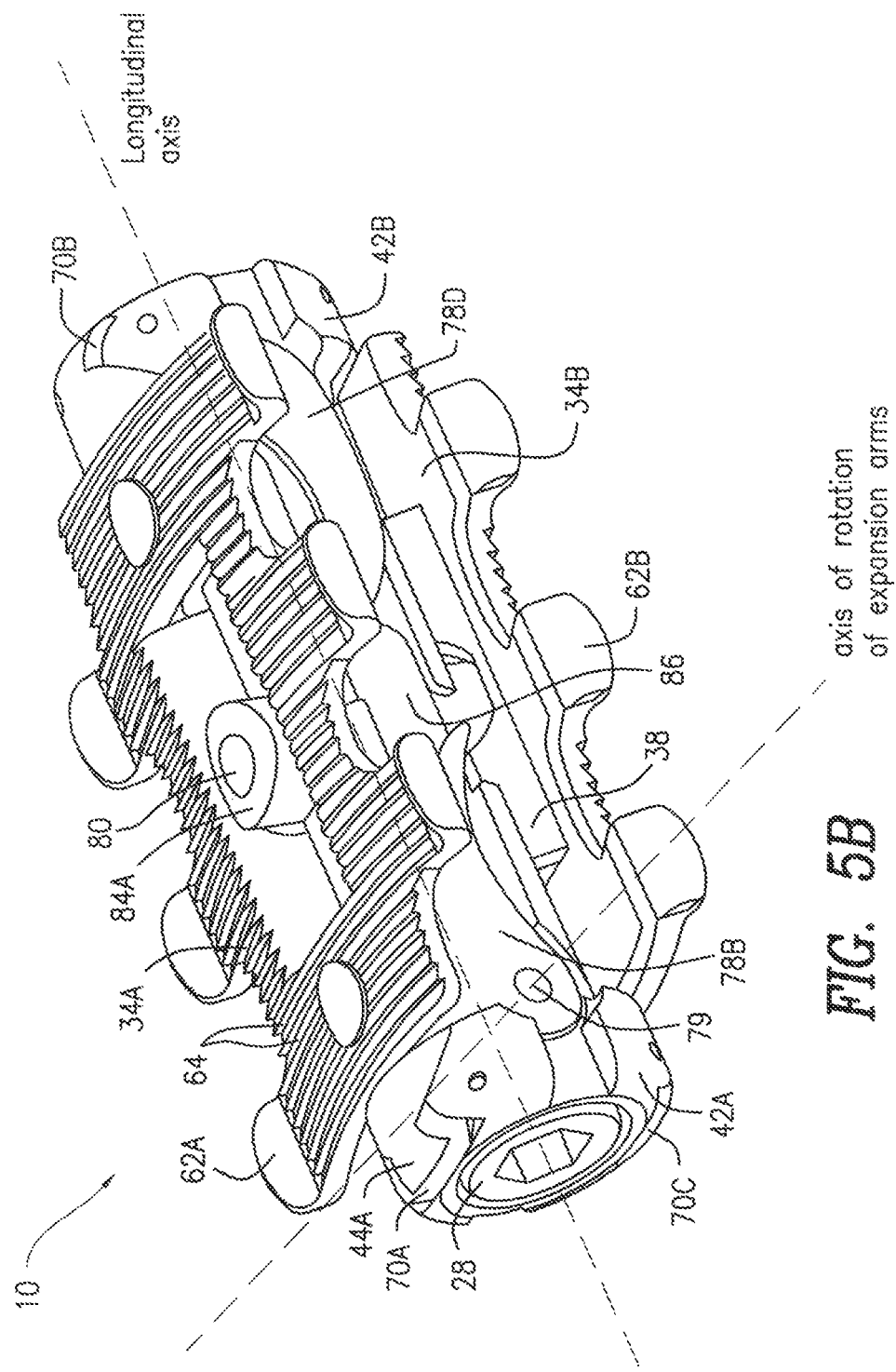
FIG. 5B shows the fourth embodiment of a spine cage in a partially expanded state.
Figure 5C:
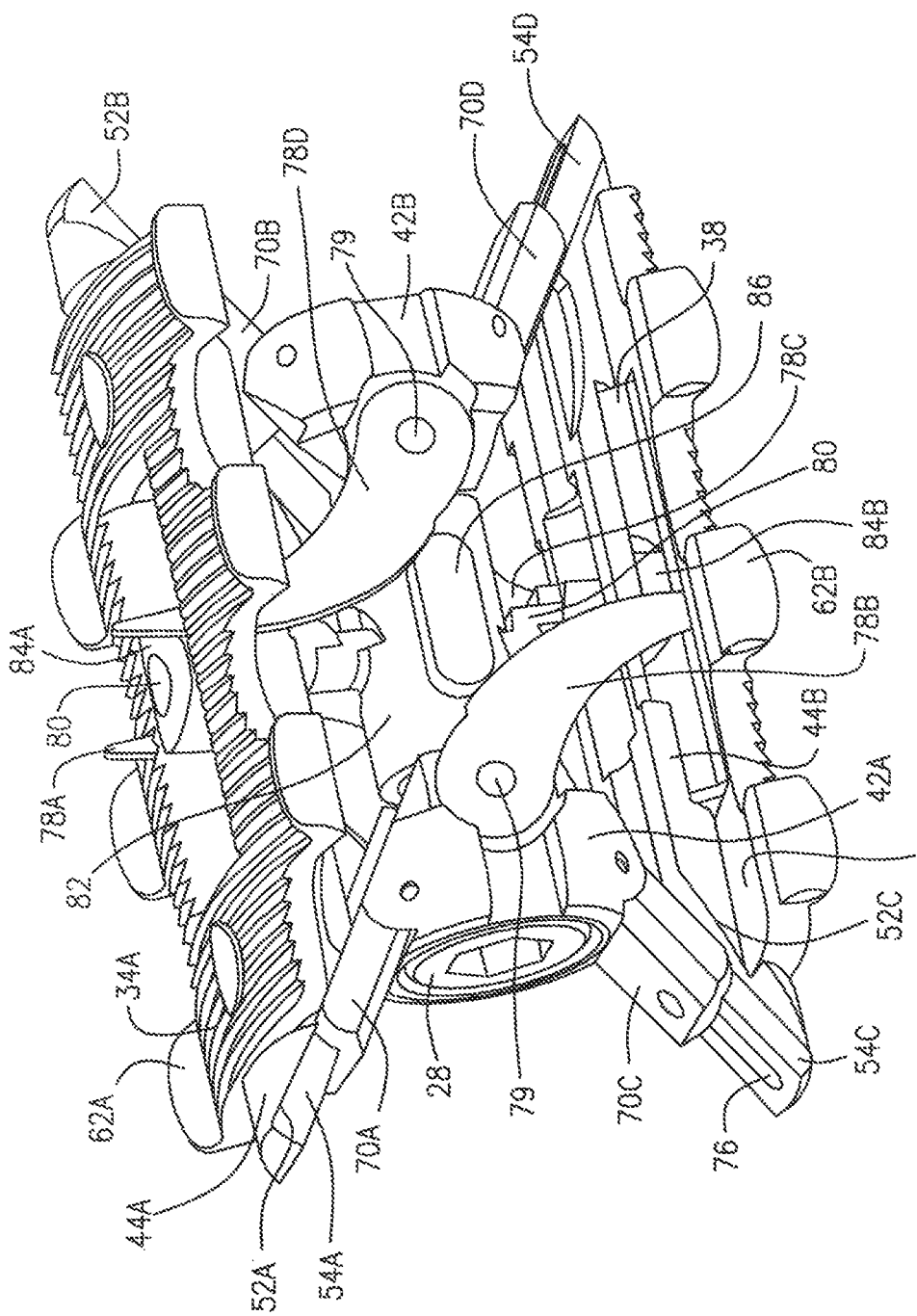
FIG. 5C shows the fourth embodiment of a spine cage in a fully expanded state.

Referring now to FIGS. 5A-5C, a fourth embodiment of a spine cage 10 is shown. As shown in FIG. 5A, the spine cage 10 may be deliverable to an intervertebral space in an unexpanded configuration. In this configuration, the spine cage 10 may have a substantially tubular shape, with the outer platforms 34A, 34B being in a deformed position with greater curvature and substantially wrapping around the other components of the device. Thus, as is shown and described in the other embodiments, the spine cage 10 is deliverable in a configuration having a reduced diameter, which reduces the amount of anatomical manipulation required for implantation. As is similar to the spine cage 10 shown and described in FIG. 4, the outer platforms 34A, 34B of the spine cage 10 shown in FIGS. 5A-5C may each include a plurality of fingers 62 that are complementary to the fingers 62 of the other platform 34. Further, each platform 34A, 34B may include a ridged or corrugated pattern 64 to enhance contact between the platforms 34A, 34B and adjacent vertebral endplates.

Referring now to FIG. 5B, the spine cage 10 is shown in an expanded state. As shown, the shape memory platforms 34A, 34B may be manufactured such that the platforms have an original position as shown in the expanded configuration of FIGS. 5B and 5C, and a deformed position with greater curvature, as shown in the unexpanded configuration of FIG. 5A. Once the spine cage 10 has been inserted in the intervertebral space 18, the higher body temperature of the surrounding area may be above the transformation temperature of the shape memory material, thereby causing the platforms 34A, 34B to flatten out and/or unfold. The functionality of the spine cage 10 of FIGS. 5A-5C may be generally similar to that of the spine cage 10 shown and described in FIGS. 2A-4. Specifically, rotation of the expansion screw 28 may cause the two wedges 42A, 42B to be drawn toward each other, which, in turn, causes the expansion bodies 44A, 44B to move away from each other. However, the spine cage 10 of FIGS. 5A and 5C may further include expansion arms 78A, 78B, 78C, 78D that are each rotatably connected to a wedge 42A, 42B at a connection point 79. As shown in FIGS. 5B and 5C, for example, the first wedge 42A may include a first 78A and second 78B expansion arm, and the second wedge 42B may likewise include a first 78C and second 78D expansion arm. Each expansion arm 78 may be connected to the corresponding wedge 42 such that the expansion arm 78 is rotatable about an axis that is substantially orthogonal to the longitudinal axis of the spine cage 10. The spine cage 10 may further include a central post 80 and a central post base 82, and each expansion body 44, 44B may include a central post conduit 84A, 84B. The first 42A and second 42B wedges, first 44A and second 44B expansion bodies, the central post 80, and central post base 82 may together make up the core member 58.

Referring now to FIG. 5C, the spine cage 10 is shown in a fully expanded state. As is shown and described, for example, in FIGS. 3A, and 3B, rotation of the expansion screw 28 may cause the wedges 42A, 42B to be drawn toward each other, the expansion bodies 44A, 44B are distracted from each other, thus expanding the spine cage 10. Movement of the wedges 42A, 42B relative to the diagonal portions 52A-52D of the expansion bodies 44A, 44B may cause movement of the locking components 70A-70D likewise. For example, the diagonal portion flange 54A-54D of each expansion body 44A, 44B may include a groove 76, and at least a portion of each locking component 70A-70D may be slidably disposed aver at least a portion of the corresponding flange 54A-54D and within a corresponding groove 76. Although elements 70A-70D are referred to as locking components, it will be understood that, in any configuration of the spine cage 10, that whereas locking components 70A-70D may function to lock the wedges 42A, 42B in place, they may additionally or alternatively function to distract the expansion bodies 44A, 44B beyond that distance possible by use of the wedges 42A, 42B alone. That is, the wedges 42A, 42B may be drawn toward each other to a point that is inside of the diagonal portions 52A-52D of the expansion bodies 44A, 44B, and the locking components 70A-70D may instead remain in contact with the diagonal portions 52A-52D, thereby continuing to distract the expansion bodies 44A, 44B (for example, as is shown in FIG. 5C).

Continuing to refer to FIG. 5B, the central post 80 may extend between the first 34A and second 34B outer platforms, in a direction that is substantially orthogonal to the longitudinal axis of the spine cage 10. When the spine cage 10 is in an unexpanded state (as shown in FIG. 5A) or a partially expanded state (as shown in FIG. 5B), one end of the central post 80 may be slidably disposed within the post conduit 84A of the first outer platform 34A and the other end of the central post 80 may be slidably disposed within the post conduit 84B of the second outer platform 34B. Further, the central post 80 may be coterminous with the central post conduits 84A, 84B, as shown, for example, in FIGS. 5A and 5B. As the expansion bodies 44A, 44B are distracted from each other by rotation of the expansion screw 28, the platforms 34A, 34B and expansion bodies 44A, 44B may also move toward the ends of the central post 80, such that the central post 80 becomes recessed within the central post conduits 84A, 84B (as shown in FIG. 5C). The central post base 82 may define the minimum distance between the two wedges 42A, 42B. That is, as the wedges move toward each other with rotation of the expansion screw 28, they may come in contact with the central post base 82 and thus be prevented from moving closer together. This may help ensure that the expansion bodies 44A, 44B do not move so far away from each other that the central post 80 comes free of the central post conduits 84A, 84B.

The central post base 82 may include a protrusion 86 on either side. The expansion arms 78A-78D may have at least one curved edge that is in contact with at least a portion of a protrusion 86 as the wedges 42A, 42B move toward and away from each other. As is shown in FIG. 5B, the expansion arms 78 may be sickle-shaped, defining a wider base portion that is coupled to one of the wedges 42, and a narrower, pointed tip portion. A portion of the tip of each expansion arm 78A-78D may be in contact with a protrusion 86, whereas a portion of each expansion arm 78A-78D that is closer to the attachment point 79 may be in contact with a protrusion 86 when the spine cage 10 is in a fully expanded state. As the wedges 42A, 42B and, therefore, the expansion arms 78A-78D are drawn toward each other, the movement of the protrusions 86 along the expansion arms 78A-78D causes the expansion arms to rotate at the connection point 79 toward the outer platforms 34A, 34B. As is shown in FIG. 5C, one of the arms 78A, 78D connected to each wedge 42A, 42B on opposing sides of the device 10 may extend at least partially through an opening 88A in the first outer platform 34A. Likewise, one of the arms 78B, 78C connected to each wedge 42A, 42B on opposing sides of the device 10 may extend at least partially through an opening 88B in the second outer platform 34B. Expansion of the spine cage 10 may occur once the spine cage is in the intervertebral space 18. As they extend through the openings 88A, 88B, the pointed tips of the expansion arms 78A-78D may dig into or otherwise contact and help anchor the spine cage 10 to the endplates of adjacent vertebrae. Further, as the outer platforms 34A, 34B expand, the fingers 62A, 62B and the ridged or corrugated pattern 68 of the platforms 34A, 34B may also engage the endplates of adjacent vertebrae.

Figure 6A:
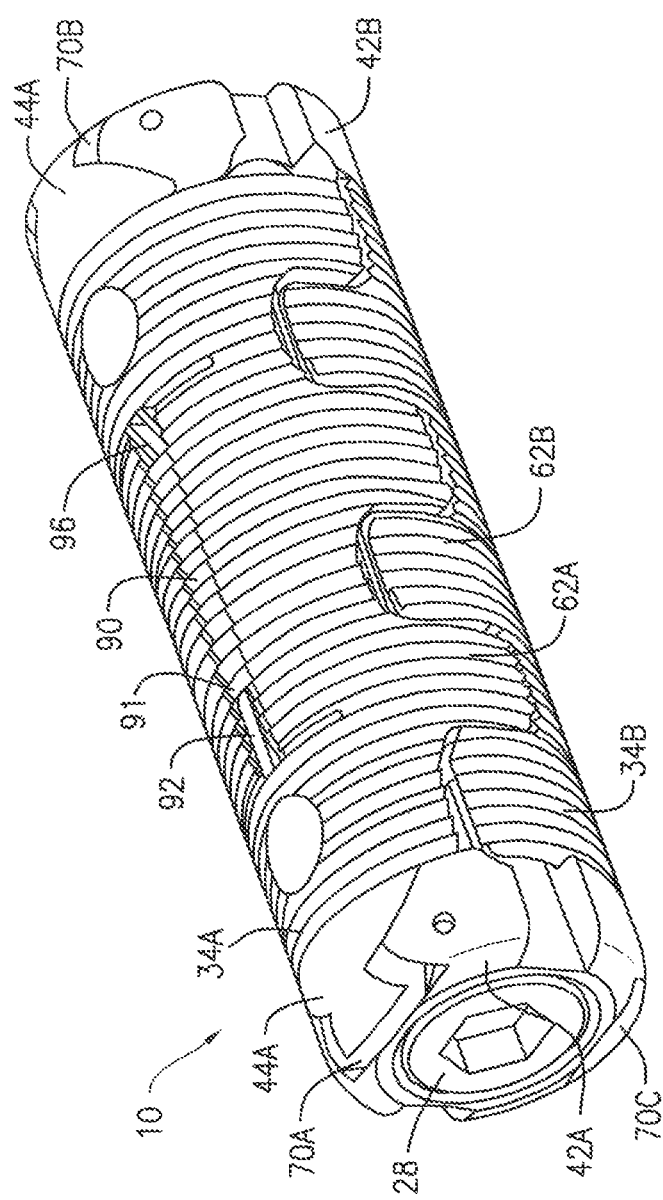
FIG. 6A shows a fifth embodiment of a spine cage in an unexpanded state.
Figure 6B:
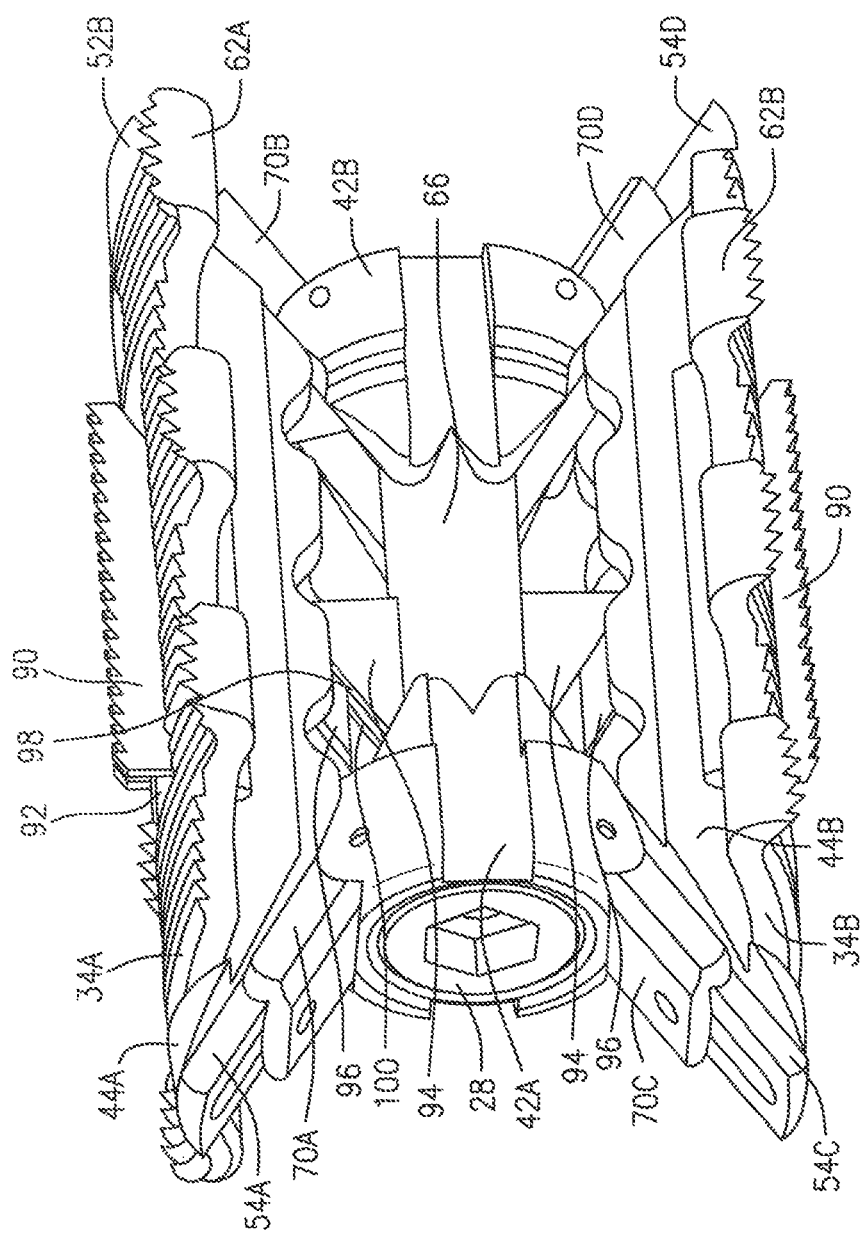
FIG. 6B shows the fifth embodiment of a spine cage in a fully expanded state.

Referring now to FIGS. 6A and 6B, a fifth embodiment of a spine cage 10 in an unexpanded state and a fully expanded state is shown. As shown in FIG. 6A, the spine cage 10 may be deliverable to an intervertebral space in an unexpanded configuration. In this configuration, the spine cage 10 may have a substantially tubular shape, with the outer platforms 34A, 34B being in a deformed position with greater curvature and substantially wrapping around the other components of the device (as shown in FIG. 6A). Thus, as is shown and described in the other embodiments, the spine cage 10 is deliverable in a configuration having a reduced diameter, which reduces the amount of anatomical manipulation required for implantation. As is similar to the spine cage 10 shown and described in FIGS. 4-5C, the outer platforms 34A, 34B of the spine cage 10 shown in FIGS. 6A and 6B may each include a plurality of fingers 62 that are complementary to the fingers 62 of the other platform 34. Further, each platform 34A, 34B may include a ridged or corrugated pattern 64 to enhance contact between the platforms 34A, 34B and adjacent vertebral endplates.

Referring now to FIG. 6B, the spine cage 10 is shown in a fully expanded state. As shown, the shape memory platforms 34A, 34B may be manufactured such that the platforms have an original position as shown in the expanded configuration of FIG. 6B, and a deformed position with greater curvature, as shown in the unexpanded configuration of FIG. 6A. Once the spine cage 10 has been inserted in the intervertebral space 18, the higher body temperature of the surrounding area may be above the transformation temperature of the shape memory material, thereby causing the platforms 34A, 34B to flatten out and/or unfold. The functionality of the spine cage 10 of FIGS. 6A and 6B may be generally similar to that of the spine cage 10 shown and described in FIGS. 2A-5C. Specifically, rotation of the expansion screw 28 may cause the two wedges 42A, 42B to be drawn toward each other, which, in turn, causes the expansion bodies 44A, 44B to move away from each other. Like the spine cage 10 shown and described in FIG. 4, the spine cage 10 in FIGS. 6A and 6B may include a core member 58 that includes two wedges 42A, 42B, each of which being engageable with the expansion screw 28, and a sleeve portion 68. At least one wedge 42A, 42B may include the sleeve portion 68 that extends from the wedge (for example, 42B, as shown in FIG. 6B) over at least a portion of the expansion screw 28. The spine cage 10 may further include locking components 70A-70D that are engageable with the expansion bodies 44A, 44B and the wedges 42A, 42B, as shown and described, for example, in FIGS. 4-5C.

Referring now to FIG. 6B, rotation of the expansion screw 28 may cause the wedges 42A, 42B to be drawn toward each other, thus causing the expansion bodies 44A, 44B to be distracted from each other, expanding the spine cage 10. Movement of the wedges 42A, 42B relative to the diagonal portions 52A-52D of the expansion bodies 44A, 44B may cause movement of the locking components 70A-70D likewise. For example, the diagonal portion flange 54A-54D of each expansion body 44A, 44B may include a groove 76, and at least a portion of each locking component 70A-70D may be slidably disposed over at least a portion of the corresponding flange 54A-54D and within a corresponding groove 76.

Continuing to refer to FIG. 6B, the spine cage 10 may include two or more tissue engagement elements 90 (for example, vertebral engagement elements) that each extend through a corresponding opening in outer platforms 34A, 34B as the device 10 is transitioned from a non-expanded configuration to an expanded configuration. Each tissue engagement element 90 may include a notch 91 that is sized to accommodate a ridge 92 in the corresponding expansion body 44A, 44B. The sleeve 68 may include expansion guides 94, each of which extending in opposite directions from the sleeve 68 toward one or the other of the outer platforms 34A, 34B. As a non-limiting example, the expansion guides 94 may each have a substantially triangular shape (for example, a right triangle as shown in FIG. 6B), the base of which being coupled to or integrated with the sleeve 68. Further, a center expansion arm 96 may be hingedly connected to each tissue engagement element 90, such that the center expansion arms 96 are folded against the engagement elements 90, outer platforms 34A, 34B, and/or the expansion bodies 44A, 44B when the device 10 is in the unexpanded configuration. When the device 10 is in an expanded configuration, the center expansion arms 96 may hinge inward, toward the sleeve 68.

Each expansion guide 94 may include a substantially diagonal edge 98 and a slot 100 within each expansion guide 94. As shown in FIG. 6B, the diagonal edge may face the wedge 42 to which the sleeve 68 is not attached. For example, if the sleeve 68 is attached to the second wedge 42B, the diagonal edge 98 may be on the side of the expansion guide 94 that faces the first wedge 42A. Each center expansion arm 96 may be received within a corresponding slot 100 when the spine cage 10 is in an expanded configuration. At least a portion of each slot 100 may substantially parallel to the diagonal edge 98, such that movement of the wedges 42A, 42B toward each other advances at least a portion of each center expansion arm 96 along the slot 100, from the sleeve 68 toward the outer platforms 34A, 34B. This, in turn, may cause the tissue engagement elements 90 to extend beyond the outer platforms, 34A, 34B (that is, distally from the sleeve 68 and screw 28 beyond the outer platforms 34A, 34B). Thus, as the expansion bodies 44A, 44B are distracted from each other by rotation of the expansion screw 28, the platforms 34A, 34B and expansion bodies 44A, 44B extension of the tissue engagement elements 90 toward each of the adjacent vertebrae may enhance contact between the spine cage 10 and the adjacent vertebrae.

Figure 7A:
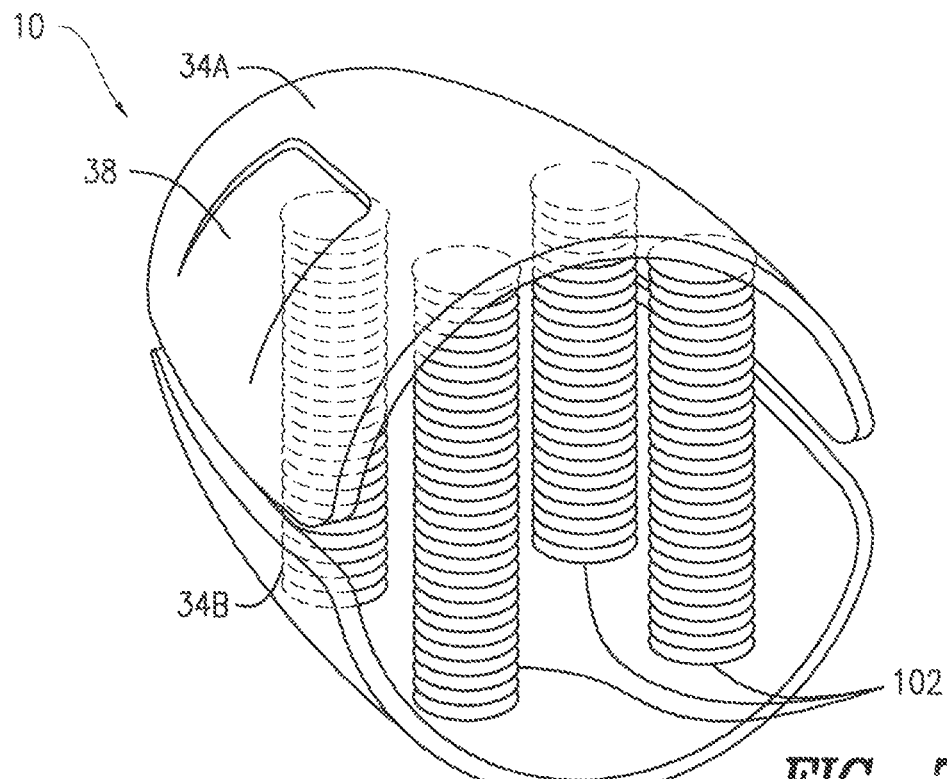
FIG. 7A shows a sixth embodiment of a spine cage in an unexpanded state.
Figure 7B:
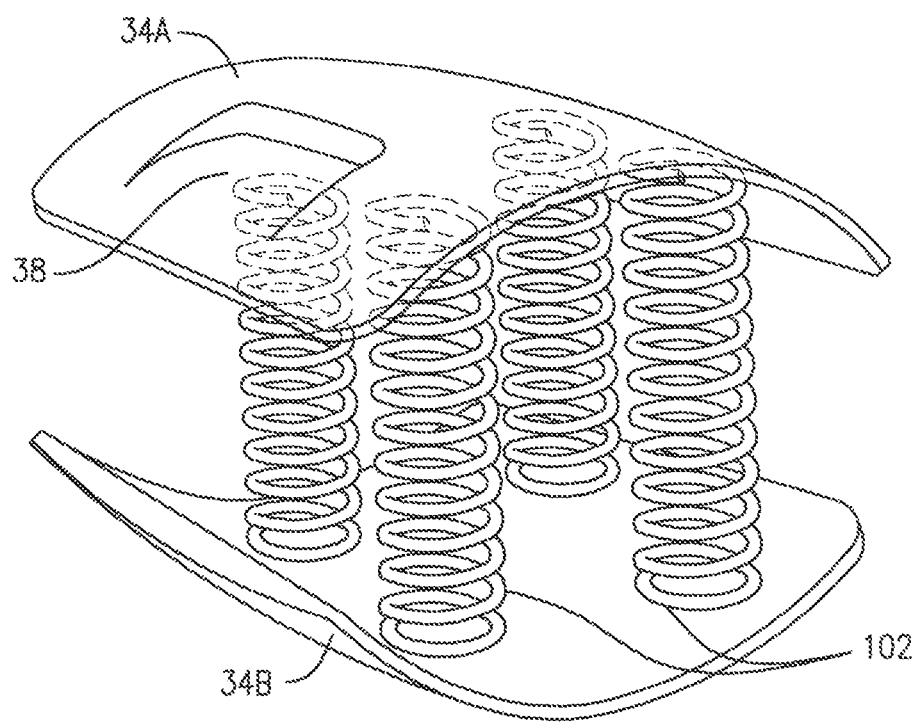
FIG. 7B shows the sixth embodiment of a spine cage in a fully expanded state.

Referring now to FIGS. 7A and 7B, a sixth embodiment of a spine cage 10 in an unexpanded state and an expanded state is shown. The spine cage 10 may generally include first 34A and second 34B outer shape memory platforms and a plurality of shape memory coils 102 between the outer platforms 34A, 34B. The shape memory platforms 34A, 34B may be manufactured such that the platforms have an original position as shown in the expanded configuration of FIG. 7B, and a deformed position with greater curvature, as shown in the unexpanded configuration of FIG. 7A. Likewise, the plurality of shape memory coils 102 may be manufactured such that each coil has an original extended position as shown in the expanded configuration of FIG. 7B, and a deformed, retracted position as shown in the unexpanded configuration of FIG. 7A. The stiffness value of the shape memory material from which the coils are manufactured may be such that the coils 102 behave in a spring-like manner once implanted (that is, the shape memory coils may be flexible enough that they are able to compress, extend, and bend like a conventional spring). In the unexpanded configuration, each of the plurality of coils 102 may be retracted and the outer platforms 34A, 34B may be curved about the plurality of coils 102. In the expanded configuration, each of the plurality of coils 102 may be extended and the outer platforms 34A, 34B may be expanded. The spine cage of FIGS. 7A and 7B may preserve the patient's range of spinal motion and provide a natural disc response.

Figure 8:
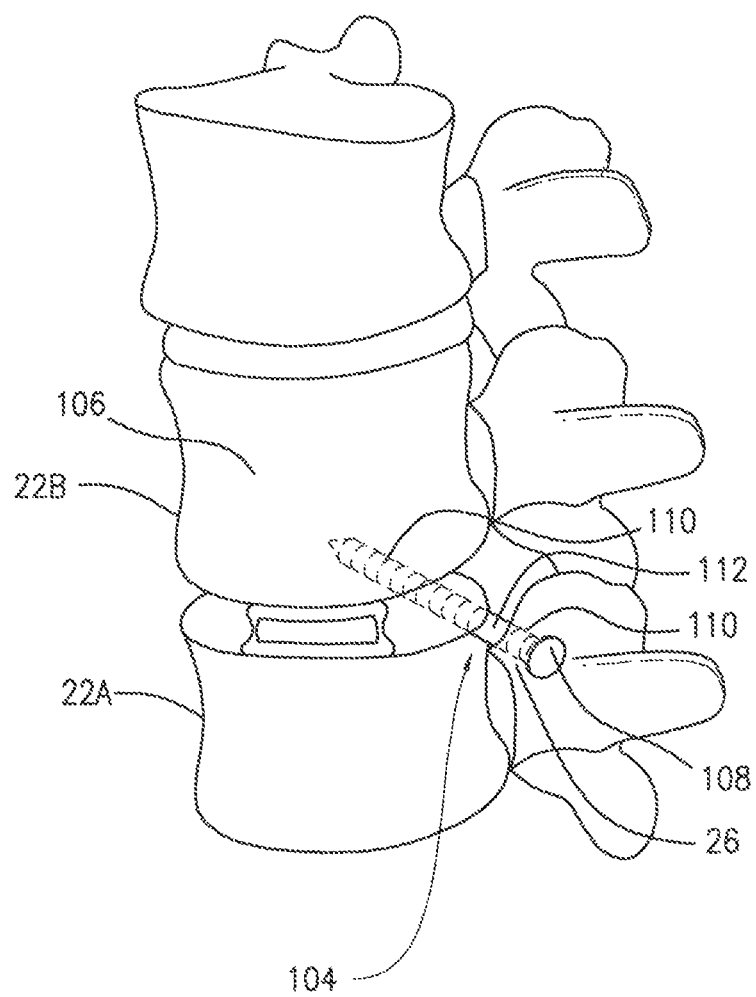
FIG. 8 shows a view of low-profile transvertebral screws inserted between adjacent vertebrae.

Referring now to FIG. 8, a view of low-profile transvertebral screws 104 inserted between adjacent vertebrae 22 is shown. Such screws 104 may be used to supplement a procedure such as an interbody fusion procedure. As shown in FIG. 8, a screw 104 may be inserted into a pedicle 26 of one vertebra 22A and into the vertebral body 106 of an adjacent vertebra 22B. The head 108 of the low-profile screw 104 may be countersunk into the pedicle 26 so that no or a minimal portion thereof is exposed. Further, the screw 104 may include two discrete threaded portions 110 with an unthreaded portion 112 therebetween. This prevents injury to disc or other intervertebral tissue by the screw threading when the screws are in place. The surgeon may be provided with a variety of screws, each having a different distance that is unthreaded. The required unthreaded distance may be determined for each patient (such as by MRI imaging or the like) and the appropriate screw selected for use.

It will be understood that the devices, systems, and methods described herein may be suitable for a variety of spinal procedures, including a lateral transpsoas retroperitoneal approach (in which the devices shown and described herein may allow for substantially less risk of lumbo-sacral plexus injury and to associated neurological injuries), a unilateral or bilateral transforamenal approach (in which devices shown and described herein may allow for an intervertebral reduction, with minimal nerve retraction, bone removal, musculoskeletal or ligamental injury while maximizing intervertebral three-dimensional reconstruction and reduction), and a transpedicular transvertebral approach (in which the devices shown and described herein may cause no segmental intervertebral musculoskeletal damage at all, may preserve the facet joints and the muscular attachments, may maximize ligament strength, and may spare the peripheral disc annulus and capsule while enabling a broad intradiscal expansion, which may serve as the basis for an intervertebral fusion or motion preserving intervertebral memory coil device, acting as disc arthroplasty).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An intervertebral medical device, the medical device comprising:
   a core member;
   a first outer plate and a second outer plate, each of the first and second outer plates being coupled to at least a portion of the core member, wherein the first and second outer plates are composed of a shape memory material, the first and second outer plates being transitionable between a non-expanded, substantially tubular configuration and an expanded, substantially planar configuration;
   a first tissue engagement element coupled to at least a portion of the core member, wherein the first tissue engagement element extends through an opening in the first outer plate when the first outer plate is in the expanded, substantially planar configuration; and
   a rotational screw mechanism at least partially disposed within the core member and operable to selectively adjust a distance between the first and second outer plates.

2. The medical device of claim 1, further comprising a second tissue engagement element coupled to at least a portion of the core member, wherein the second tissue engagement element extends through an opening in the second outer plate when the second outer plate is in the expanded, substantially planar configuration.

3. The medical device of claim 2, wherein each of the first and second tissue engagement elements include an elongated body having a plurality of ridges thereon.

4. The medical device of claim 1, wherein a distance between the first and second outer plates can be selectively adjusted to increase or decrease an overall height of the medical device.

5. The medical device of claim 1, wherein the rotational screw mechanism is operable to extend the first tissue engagement element through the opening in the first outer plate.

6. The medical device of claim 1, wherein the first and second outer plates transition to the expanded configuration when the temperature of the first and second outer plates is greater than a transformative temperature of the shape memory material.

7. The medical device of claim 6, wherein the transformative temperature is less than the human body temperature of approximately 37 degrees Celsius.

8. An intervertebral medical device, the medical device comprising:
   a core member;
   a first outer plate and a second outer plate, each of the first and second outer plates being coupled to at least a portion of the core member, wherein the first and second outer plates are composed of a shape memory material, the first and second outer plates being transitionable between a non-expanded, substantially tubular configuration and an expanded, substantially planar configuration;
   a first tissue engagement element coupled to at least a portion of the core member, wherein the first tissue engagement element extends through an opening in the first outer plate when the first outer plate is in the expanded, substantially planar configuration; and
   at least one locking component configured to maintain a distance between the first and second outer plates in the expanded, substantially planar position.

9. The medical device of claim 8, wherein the at least one locking component is mechanically actuated by a rotational screw mechanism.

10. The medical device of claim 1, further comprising a plurality of fingers extending from a circumference of each of the first and second outer plates configured to anchor the medical device to adjoining vertebral tissue.

11. A medical device for insertion between two adjacent vertebrae, the device comprising:
    a first outer platform and a second outer platform, wherein a distance between the first and second outer platform is selectively adjustable to increase or decrease an overall height of the medical device, wherein each of the first and second outer platforms is composed of a shape-memory material having a transformative temperature, the device having a first, substantially tubular configuration at a first temperature less than the transformative temperature and having a second configuration different from the first configuration at a second temperature greater than the transformative temperature, and
    a first tissue engagement element coupled to the first outer platform, wherein the first tissue engagement element defines a ridged surface that is substantially coincident with an outer surface of the first outer platform in the first configuration, and wherein the first tissue engagement element extends through an opening in the first outer platform when the first outer platform is in the second configuration.

12. The medical device of claim 11, wherein the transformative temperature is less than the human body temperature of approximately 37 degrees Celsius.

13. The medical device of claim 11, further comprising at least one locking component configured to maintain at least one of the first and second outer platforms in the second configuration, wherein the at least one locking component is mechanically actuated by a rotational screw mechanism.

14. A method of implanting a medical device, comprising:
   implanting the medical device between two vertebral bodies, wherein the medical device comprises:
      a core member;
      a first outer plate and a second outer plate, each of the first and second outer plates being coupled to at least a portion of the core member, wherein the first and second outer plates are composed of a shape memory material having a transformative temperature, wherein the first and second outer plates transition from a non-expanded, substantially tubular configuration to an unfurled, substantially planar configuration at the transformative temperature; and
      a first tissue engagement element coupled to at least a portion of the core member, wherein the first tissue engagement element extends through an opening in the first outer plate when the first outer plate is in the expanded, substantially planar configuration;
   wherein implanting the medical device results in the first and second outer plates transitioning from the non-expanded, substantially tubular configuration to the unfurled, substantially planar configuration;
   selectively adjusting a distance between the first and second outer plates to increase or decrease an overall height of the medical device, wherein selectively adjusting a distance between the first and second outer plates includes rotationally engaging a portion of the medical device with an external instrument.

15. The method of claim 14, further comprising engaging a locking element of the medical device to prevent the first and second outer plates from moving towards each other.

16. A method of implanting a medical device, comprising:
   implanting the medical device between two vertebral bodies, wherein the medical device comprises:
      a core member;
      a first outer plate and a second outer plate, each of the first and second outer plates being coupled to at least a portion of the core member, wherein the first and second outer plates are composed of a shape memory material having a transformative temperature, wherein the first and second outer plates transition from a non-expanded, substantially tubular configuration to an unfurled, substantially planar configuration at the transformative temperature; and
      a first tissue engagement element coupled to at least a portion of the core member, wherein the first tissue engagement element extends through an opening in the first outer plate when the first outer plate is in the expanded, substantially planar configuration; and
   mechanically reinforcing the first and second outer plates in the unfurled, substantially planar configuration.

* * * * *